US010653718B2

(12) United States Patent
Joanny Menvielle-Bourg

(10) Patent No.: US 10,653,718 B2
(45) Date of Patent: May 19, 2020

(54) COMPOSITION FOR THE ORAL ADMINISTRATION OF MAGNESIUM, IN ASSOCIATION WITH A COMPOSITION FOR TREATING TYPE 2 DIABETES OR THE COMPLICATIONS THEREOF

(71) Applicant: Fabienne Joanny Menvielle-Bourg, Cannes (FR)

(72) Inventor: Fabienne Joanny Menvielle-Bourg, Cannes (FR)

( * ) Notice: Subject to any disclaimer, the term of this patent is extended or adjusted under 35 U.S.C. 154(b) by 0 days.

(21) Appl. No.: 14/897,737

(22) PCT Filed: Jun. 3, 2014

(86) PCT No.: PCT/EP2014/061518
§ 371 (c)(1),
(2) Date: Dec. 11, 2015

(87) PCT Pub. No.: WO2014/198591
PCT Pub. Date: Dec. 18, 2014

(65) Prior Publication Data
US 2016/0120900 A1    May 5, 2016

(30) Foreign Application Priority Data

Jun. 11, 2013   (EP) .................................... 13305789

(51) Int. Cl.
| A61K 33/06 | (2006.01) |
| A61K 45/06 | (2006.01) |
| A61K 9/20 | (2006.01) |
| A61K 9/28 | (2006.01) |
| A61K 33/14 | (2006.01) |
| A61K 33/08 | (2006.01) |

(52) U.S. Cl.
CPC ............ *A61K 33/06* (2013.01); *A61K 9/2009* (2013.01); *A61K 9/2013* (2013.01); *A61K 9/2018* (2013.01); *A61K 9/2054* (2013.01); *A61K 9/2072* (2013.01); *A61K 9/28* (2013.01); *A61K 9/288* (2013.01); *A61K 9/2866* (2013.01); *A61K 9/2886* (2013.01); *A61K 33/08* (2013.01); *A61K 33/14* (2013.01); *A61K 45/06* (2013.01)

(58) Field of Classification Search
CPC .............. A61K 2300/00; A61K 31/155; A61K 31/175; A61K 31/426; A61K 31/555; A61K 33/24; A61K 45/06
See application file for complete search history.

(56) References Cited

U.S. PATENT DOCUMENTS

| 6,376,549 B1 * | 4/2002 | Fine ..................... A61K 31/155 424/617 |
| 8,399,017 B2 | 3/2013 | Joanny |
| 2011/0091548 A1 | 4/2011 | Joanny |

FOREIGN PATENT DOCUMENTS

WO    WO 2009/150323    12/2009

OTHER PUBLICATIONS

Moran et al. "Oral Magnesium Supplementation Improves Insulin Sensitivity and Metabolic Control in Type 2 Diabetic Subjects", Diabetes Care, vol. 26, No. 4, 1147-1152, published Apr. 2003.*
WO2009150323A1 to Joanny, translation, published Dec. 17, 2009.*
Garber, A.J., "Magnesium Utilization Survey in Selected Patients with Diabetes," *Clinical Therapeutics*, 1996, vol. 18, No. 2, pp. 285-294.
Sales, C.H., et al., "Magnesium and diabetes mellitus: Their relation," *Clinical Nutrition*, 2006, vol. 25, No. 4, pp. 554-562.
Song, Y., et al., "Effects of oral magnesium supplementation on glycaemic control in Type 2 diabetes: a meta-analysis of randomized double-blind controlled trials," *Diabetic Medicine*, 2006, vol. 23, No. 10, pp. 1050-1056.
Written Opinion in International Application No. PCT/EP2014/061518, dated Jul. 8, 2014, pp. 1-7.

* cited by examiner

*Primary Examiner* — Audrea B Coniglio
*Assistant Examiner* — Audrea Buckley
(74) *Attorney, Agent, or Firm* — Saliwanchik, Lloyd & Eisenschenk

(57) ABSTRACT

The invention relates to a specific composition for oral administration of magnesium, for use in the treatment of type 2 diabetes or the complications thereof, in association with a composition for treating type 2 diabetes or the complications thereof.

15 Claims, 1 Drawing Sheet

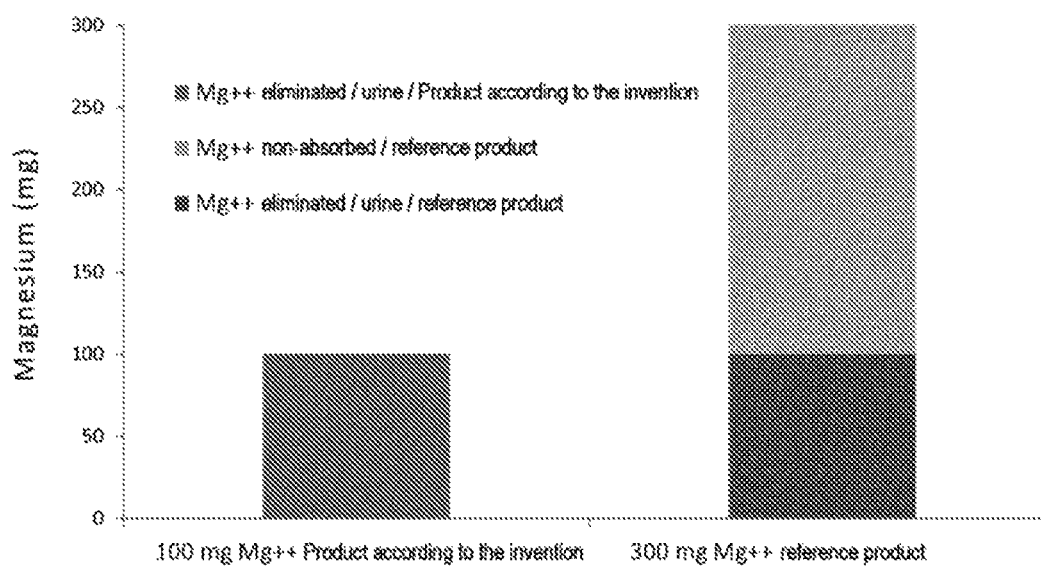

COMPOSITION FOR THE ORAL ADMINISTRATION OF MAGNESIUM, IN ASSOCIATION WITH A COMPOSITION FOR TREATING TYPE 2 DIABETES OR THE COMPLICATIONS THEREOF

CROSS-REFERENCE TO RELATED APPLICATION

This application is the U.S. national stage application of International Patent Application No. PCT/EP2014/061518, filed Jun. 3, 2014.

FIELD OF THE INVENTION

The present invention relates to a composition for oral administration, comprising magnesium, for use in the treatment of type 2 diabetes or complications thereof, in combination with a composition intended for treating type 2 diabetes or complications thereof. The composition comprising magnesium is more specifically in the form of a sustained- and continuous-release tablet.

PRIOR ART

It is known, in particular from patent applications WO 01/22943, U.S. Pat. Nos. 6,887,492, 5,849,338 and GB 1356097 illustrating the prior art, that technical solutions intended to provide magnesium with delayed release over time have already been proposed in the past.

Moreover, with regard to sustained-release oral magnesium compositions, European patent EP 0 542 979 and international applications WO 2004/105778 and WO 2009/150323 are known.

Magnesium, in hydrate, hydrated oxide, carbonate, chloride and other salt forms, is widely used in the form of food supplements and medicaments. The magnesium ion $Mg^{2+}$ plays a very important role in the ion balance of the human body; in particular it plays a role in many enzymatic reactions involved in metabolic processes in humans. The magnesium levels in the plasma of individuals in good health are relatively constant, with a reference range for total serum levels of 0.75-0.96 mmol/l. A certain number of hormones, including parathyroid hormone (PTH) and calcitonin, vitamin D, glucagon, antidiuretic hormone, aldosterone, sex steroids and insulin, have been described as influencing the magnesium balance (N E Saris et al. Magnesium. An Update on Physiological, Clinical and Analytical Aspects, Clinica chimica acta; International Journal of Clinical Chemistry, 294 (2000), 1-26). Insulin stimulates the renal reabsorption of magnesium in the ascending branch of the loop of Henle. Thus, insulin deficiency directly affects magnesium transport in addition to developing ketoacidosis which inhibits magnesium storage (G A Quamme, Renal Magnesium Handling: New Insights in Understanding Old Problems, Kidney International, 52 (1997), 1180-1195).

Many disorders may be associated with a lack of magnesium: depression and anxiety, diabetes, muscle spasms, cramps, cardiovascular disorders, high arterial pressure, insomnia and osteoporosis. Magnesium actively participates in the transmission of nerve influxes between neurons. The recommended daily intake of magnesium in Europe is estimated at 375 mg per day (double for sportsmen and sportswomen or pregnant women) or alternatively approximately 6 mg per kg of body weight.

It is common to take magnesium supplements in the form of medicaments or food supplements. These use various salts (for example, chloride, carbonate, pidolate, aspartate, citrate, lactate, malate, threonate) or oxides and are provided in various galenical forms (for example, solution, gel capsule, tablet) with one or more of these salts in their composition. These various galenical forms on the market may provide various types of release of the magnesium in the organism: immediate release, delayed release or sustained release.

The body does not produce magnesium. It consumes it more or less quickly depending on physical activity and stress. It must therefore take it from the daily diet and from supplements to this diet if necessary. Excessive consumption of magnesium is naturally eliminated by the organism in the urine. Magnesium does not therefore accumulate. The ingestion of large amounts of magnesium causes a laxative, or even purgative, effect. Poisoning caused by excess magnesium can occur in children and in the case of an individual suffering from renal failure.

Diabetes mellitus or more generally diabetes is a disease caused by a deficiency or a decrease in the efficiency of indigenous insulin. This metabolic disease is characterized by a high sugar or glucose level in the blood, either because the pancreas does not produce enough insulin (type 1 diabetes) or because the cells do not respond correctly to the insulin produced (type 2 diabetes).

Numerous results suggest that a higher magnesium intake can reduce the incidence of diabetes. A meta-analysis carried out by Dong et al. has made it possible to provide evidence that magnesium intake is inversely proportional to the risk of developing type 2 diabetes, this being in a dose-dependent manner (Jia-Yi Dong et al. Magnesium intake and risk of type 2 diabetes: meta-analysis of prospective cohort studies, Diabetes Care, 34 (2011), 2116-2122). This suggests that magnesium is one of the nutritive elements involved in the prevention of diabetes. The link between magnesium and diabetes mellitus has therefore already been described. Studies have shown that the average levels of free plasma and intracellular magnesium are lower in diabetic patients than the general population. Hypomagnesemia occurs in 13.5% to 47.7% of patients with type 2 diabetes, compared to 2.5% to 15% of individuals without diabetes. Patients with diabetes mellitus often exhibit a magnesium deficiency, which might be associated with insulin resistance (characteristic of patients suffering from type 2 diabetes). It has also been noted that magnesium improves the insulin response to dietary sugar and improves the action of insulin by regulating the level of sugar in the blood.

As regards the complications of diabetes such as cardiovascular diseases, it has been shown that magnesium supplements with $MgCl_2$ make it possible to reduce blood pressure in diabetic hypertensive adults with hypomagnesemia.

As regards the retinopathy caused by diabetes, some studies have shown that patients with retinopathy exhibit an average plasma magnesium concentration which is lower than in patients without retinopathy (P McNair et al., 'Hypomagnesemia, a Risk Factor in Diabetic Retinopathy', *Diabetes,* 27 (1978), 1075-1077).

Nephropathy is one of the most frequent complications of diabetes. It has been described that relatively low magnesium levels observed in the serum may be associated with a faster decline in renal function in patients with type 2 diabetes (P C Pham et al., 'The Link Between Lower Serum Magnesium and Kidney Function in Patients with Diabetes Mellitus Type 2 Deserves a Closer Look', *Clinical nephrology,* 71 (2009), 375-379; P C T Pham et al., 'Lower Serum Magnesium Levels Are Associated with More Rapid Decline of Renal Function in Patients with Diabetes Mellitus Type 2', *Clinical nephrology*, 63 (2005), 429-436).

Researchers have shown the efficacy and innocuousness of $MgCl_2$ for treating depression in elderly patients with type 2 diabetes and hypomagnesemia (Lazaro Barragán-Rodríguez, Martha Rodriguez-Morán and Fernando Guerrero-Romero, 'Efficacy and Safety of Oral Magnesium Supplementation in the Treatment of Depression in the Elderly with Type 2 Diabetes: a Randomized, Equivalent Trial', *Magnesium research: official organ of the International Society for the Development of Research on Magnesium*, 21 (2008), 218-223).

It has also been observed that a magnesium deficiency is present and linked to the presence of foot ulcers in patients with type 2 diabetes (M Rodríguez-Morán and F Guerrero-Romero, 'Low Serum Magnesium Levels and Foot Ulcers in Subjects with Type 2 Diabetes', *Archives of medical research*, 32 (2001), 300-303).

It is therefore reasonable to think that magnesium satiety may make it possible to delay the appearance of diabetes, to reduce the effects thereof and potentially to prevent serious complications thereof, such as cardiovascular diseases, retinopathy, nephropathy, depression and foot ulcers.

Thus, a magnesium supplement in patients with type 2 diabetes could possibly be beneficial. However, long-term treatment with a high dose of magnesium can cause side effects which are clinically relevant for patient adherence, in particular in patients suffering from renal failure.

Despite the remarkable progress made in the field of diabetes and complications thereof, it remains necessary to find new treatments or drug combinations that are both effective for treating diabetes and have minimized side and/or toxic effects. Diabetes is a chronic disease which can be controlled. The disease represents a loss of freedom with a strict diet that must be followed, a loss of one's security (for example hypoglycemic attack) and unpredictable complications. In order to limit the risk of complications, it is necessary to scrupulously control one's diabetes, and to follow one's treatment and the advice of one's physician. Thus, magnesium is one of the elements which might make it possible to improve the quality of life of the diabetic patient. There are many magnesium-based formulas or compositions (medicaments or food supplements) on the current market, but they may not all be suitable for the needs of the diabetic patient.

In this respect, it has been identified by the applicant that the combination of a specific magnesium-based composition and a pharmaceutical composition comprising at least one pharmaceutical active agent for treating type 2 diabetes or complications thereof makes it possible to obtain a particularly effective therapeutic treatment for type 2 diabetes and complications thereof, without side effects associated in particular with taking magnesium. The composition described below has many advantages, since it makes it possible in particular not to interact with the diabetes treatment, to be effective in improving the physiological parameters associated with diabetes, to be used in the long term for correcting a magnesium deficiency (enabling in particular a constant Mg plasma level without blood peak), to have good bioavailability, to be well-tolerated at the intestinal level and without side effects, to have a chemical and galenical formulation which decreases Mg elimination via the kidneys, and to have a formulation which makes it possible to decrease risks of hypermagnesemia in the event of nephropathy or renal failure.

Thus, the applicant proposes a composition comprising magnesium, which is in particular a low-dose and sustained-release composition, for use in the treatment of type 2 diabetes or one of the complications thereof, in combination with a pharmaceutical composition comprising at least one active agent intended for the treatment of type 2 diabetes. Thus, the specific composition comprising magnesium makes it possible to maintain a relatively constant magnesium level in the body (for example, throughout said treatment, day and night), without causing side effects, in particular due to excessively high doses of magnesium in the blood.

Subject of the Invention

According to a first aspect of the invention, what is proposed is a composition comprising magnesium, which is in particular a low-dose and sustained-release composition, for use in the treatment of type 2 diabetes or one of the complications thereof, in combination with a pharmaceutical composition comprising at least one active agent intended for the treatment of type 2 diabetes. More specifically, said compositions are administered simultaneously, separately or in a manner spread out over time.

More specifically, the composition comprising magnesium is a composition for oral administration, in tablet form, comprising a gradual-release magnesium matrix, which forms in particular a core, said matrix comprising, or in particular consisting of, magnesium, a hydrophilic delay agent (B1), a hydrophobic delay agent (B2), an inert filler (C1) acting as a diluent and an inert filler (C2) acting as a lubricating means, said matrix being characterized in that it comprises, or in particular consists of:

(A) 90 to 110 parts by weight of magnesium, the magnesium source being present in a form chosen from MgO, $MgCl_2$ and hydrates of formula $MgCl_2.n(H_2O)$ where n is a real number greater than 0 and less than or equal to 6, (B1) 180 to 190 parts by weight of hydroxypropylmethylcellulose, (B2) 19.8 to 22.2 parts by weight of glyceryl behenate, (C1) 10 to 12 parts by weight of lactose, and (C2) 10 to 12 parts by weight of colloidal silica;

said composition also comprising a coating, which is not a gastroresistant coating, but a protective coating which slows down the dissolution of the Mg at the gastric level.

The coating of the matrix (i.e., the coating of the bare tablet) is not gastroresistant. On the one hand, it acts as protection for the matrix, in particular during packaging and storage, and on the other hand, it serves to slow down the release of the magnesium at the gastric level. According to one particular mode, it represents 15 to 75 parts by weight for an amount of 90 to 110 parts by weight of Mg (i.e., approximately 1.3% to 7.5% by weight relative to the weight of the matrix, i.e., of the bare tablet).

The degree of dissolution ($\delta$) of the magnesium (expressed as % relative to the total magnesium provided by the magnesium source) has been determined in vitro. The matrix coated according to the invention provides, after 2 h in 0.1N HCl medium, a degree of dissolution $\delta$ which is less than or equal to 60%, preferably between 20% and 60%.

When it is desired to assess the overall in vitro dissolution kinetics of a tablet, a standard system of dissolution (denoted herein "dissolution system A"), first in a 0.1N HCl acidic medium (advantageously 900 ml according to the US Pharmacopeia) from T=0 to T=2 h (i.e., treatment corresponding approximately to the transit time in the stomach), and then in a buffer (advantageously 900 ml) at pH 6.8 from T=2 h to T=8 h, is used in order to determine the cumulative contents of dissolved active substance, in this case magnesium, at the times T=2 h, T=4 h, T=6 h and T=8 h (i.e., treatment corresponding approximately to the transit time in the small intestine (from T=2 h to T=4 h), then treatment corresponding approximately to the transit in the large intestine (from T=4 h to T=8 h)). These dissolution kinetics are determined at a temperature which can be from ambient temperature (15-25° C.) up to 40° C. Since, in the present invention, the coated tablet and the constituents thereof are all stable with respect to storage for several months at 40° C., the dissolution kinetics were measured in this case at 40° C. for convenience so as to be under temperature conditions substantially similar to the temperature inside the human body.

The coated tablet used in the composition according to the invention has a dissolution profile such that:
- at T=2 h: $\delta \leq 60\%$, more specifically: $20\% \leq \delta \leq 60\%$, and preferably: $25\% \leq \delta \leq 58\%$;
- at T=4 h: $\delta \leq 85\%$, more specifically: $40\% \leq \delta \leq 85\%$, and preferably: $45\% \leq \delta \leq 82\%$;
- at T=6 h: $\delta \leq 98\%$, more specifically: $60\% \leq \delta \leq 98\%$, and preferably: $80\% \leq \delta \leq 95\%$; and
- at T=8 h: $\delta \leq 100\%$, more specifically: $90\% \leq \delta \leq 100\%$, and preferably: $95\% \leq \delta \leq 99.9\%$.

Thus, the composition comprising magnesium used in the present invention advantageously exhibits a dissolution which (i) begins in the 'gastric' phase (from T=0 to T=2 h) with slowed dissolution kinetics [the degree of dissolution ($\delta$) of the magnesium relative to the magnesium administered by means of the magnesium source being less than or equal to 60%], which enables the magnesium to arrive in a drawn-out dose in the small intestine, where it begins to be absorbed with low kinetics (from T=2 h to T=4 h) on the one hand, then to arrive at the 'large intestine' phase (from T=4 h to T=8 h), on the other hand. The composition used according to the invention therefore has the advantage of being a sustained-release composition. The term "sustained release" or "gradual release" of the magnesium therefore corresponds to a continuous release of the magnesium in biological form, the entirety being absorbed by the organism over a period of 8 hours starting from tablet ingestion.

Thus, the composition comprising magnesium has the advantage of a preferential absorption of $Mg^{2+}$ in the ileum, at which site Mg absorption is at a maximum, and a slow and gradual dissolution, which is programmed, from exiting the stomach as far as the large intestine. The release of the magnesium in the $Mg^{2+}$ form advantageously takes place continuously throughout the gastrointestinal tract from the stomach to the large intestine, while the absorption of the magnesium (still in the $Mg^{2+}$ form) takes place all along the intestinal tract from the duodenum to the large intestine, the absorption being at its maximum in the ileum (i.e., the final part of the small intestine).

According to one particular aspect of the invention, a composition is provided for oral administration of magnesium, in tablet form, with a gradual release, said composition comprising:
  a matrix (forming in particular a core) comprising:
    (A) 90 to 110 parts by weight of magnesium, the magnesium source being present in the form of a hydrate of formula $MgCl_2 \cdot n(H_2O)$ where n is a real number greater than 0 and less than or equal to 6, preferably n is between 2 and 6, and better still from 3 to 11/2, advantageously n is 6/2, 7/2, 8/2, 9/2 or 10/2, and in particular 9/2,
    (B1) 180 to 190 parts by weight of hydroxypropylmethylcellulose,
    (B2) 19.8 to 22.2 parts by weight of glyceryl behenate,
    (C1) 10 to 12 parts by weight of lactose, and
    (C2) 10 to 12 parts by weight of colloidal silica; and
  a protective coating which slows down the release of the magnesium at the gastric level, and which is not gastroresistant.

DESCRIPTION OF THE FIGURE

FIG. 1. Magnesium elimination in the urine expressed in mg over 24 h after administration of two products: a sustained-release product according to the invention (2 tablets containing 50 mg of magnesium) and an immediate-release reference product A (3 tablets containing 100 mg of magnesium).

DETAILED DESCRIPTION OF THE INVENTION

Since the absorption of the magnesium occurs all along the intestinal tract, from the duodenum to the large intestine, and is optimal in the ileum (i.e., the final part of the small intestine), the transit time varying with the type of meal, and since, in the abovementioned dissolution system A at T=2 h, there is still administered Mg which has not yet dissolved, an optimally absorbable amount of the magnesium released (in the $Mg^{2+}$ form) reaches the ileum and crosses the intestinal wall, according to the invention.

According to the invention, dissolution kinetics are obtained according to which the Mg release occurs (i) relatively slowly and (ii) gradually as soon as the 'gastric' phase occurs. These kinetics exhibit a particular dissolution, on the one hand, in the stomach (thereby prohibiting a gastroresistant film-coating) and, on the other hand, in the small intestine.

The matrix according to the invention and its coating do not comprise any product prohibited by the European and international regulations relating to food supplements. In particular, said matrix and said coating are free of PCV and polyvinylpyrrolidone.

The substance B1 is hydroxypropylmethylcellulose (HPMC). It is used here in a quality which is suitable for pharmaceutical or food use.

The substance B2 is glyceryl behenate, which is a mixture essentially consisting of behenic acid monoglyceride and diglyceride (other nomenclature: 'mono-diglyceride behenate') and is known under the European additive name 'E471'. The substance B2 is also used here in a quality which is suitable for pharmaceutical or food use.

According to the invention, the B1/B2 weight ratio is between 180/22.2=8.1/1 and 190/19.8=9.6/1. Advantageously, it is recommended that said weight ratio be between 8.5/1 and 9.3/1. Preferably, the B1/B2 weight ratio will be between 8.7/1 and 9.2/1, for example, 8.8/1, 9/1 or 9.15/1.

The lactose, constituent C1, is advantageously anhydrous. Likewise, the colloidal silica, constituent C2, is advantageously anhydrous. In practice, it is rather preferred for the C1/C2 weight ratio in the matrix of the invention to be close to 1/1 and better still equal to 1/1.

The composition comprising magnesium according to the invention may correspond to:
(I) tablets with a homogeneous structure containing all of the magnesium source, or
(II) tablets with a composite (or heterogeneous) structure comprising:
  (a) a first structure (or 'internal' core) which is gastroresistant, or housed in a gastroresistant shell, said first structure containing 80% to 40% of the magnesium provided by the magnesium source, and (b) a second structure (or 'external' layer) which is hydrophilic, which dissolves in the stomach and contains 20% to 60% of the magnesium provided by the magnesium source.

The tablets used according to the invention also comprise a coating which is not gastroresistant. It is a film coating which acts (i) to protect the constituents of the bare tablet with respect to the exterior, in particular with respect to impacts, and especially (ii) to slow down the dissolution of the Mg in the 'gastric' phase. This film coating can be made of a single layer, two layers, or even three layers. In order to limit production costs, it is possible for it to be a monolayer. However, a two-layer coating is recommended, in order to have better control of the Mg dissolution. As indicated above, the coating of the matrix generally represents 15 to 75 parts by weight for a magnesium source supplying 90 to 110 parts by weight of Mg (i.e., approximately 1.3% to 7.5% by weight relative to the weight of the matrix). Preferably, it represents 15 to 70 parts by weight, and better still 15 to 45 parts by weight, for 90 to 110 parts by weight of Mg.

The substances recommended here for the coating are shellac and film-forming cellulose ethers such as alkylcelluloses, namely more particularly the mixtures of HPMC and hydroxypropylcellulose (HPC) sold in particular under the names Nutrateric® and Opadry®. It is also possible to envision a coating consisting of a first layer of shellac and an external layer made of a mixture of alkylcelluloses.

In practice, a coating is recommended which is:
(a) a monolayer film coating of shellac (used at 50% by weight in ethanol, the solvent being removed during the film-coating), or
(b) a two-layer film coating, each layer comprising a substance chosen from shellac, cellulose ethers (in particular HPMC and HPC), and mixtures thereof.

When a two-layer coating is used, the first layer (or internal layer) generally represents 0.5% to 4% by weight relative to the weight of the matrix, and the second layer (or external layer) generally represents 0.5% to 3.5% by weight relative to the weight of said matrix, the two said layers together representing 1.3% to 7.5% by weight relative to the weight of said matrix.

According to the invention, a composition, in film-coated tablet form, which gradually and continuously releases magnesium is recommended. This composition advantageously consists of:
a matrix (constituting in particular a core) comprising:
(A) 90 to 110 parts by weight of magnesium, the magnesium source being $MgCl_2.nH_2O$, where n is a real number greater than 0 and less than or equal to 6, preferably n is between 2 and 6, and better still from 3 to 11/2, advantageously n is 6/2, 7/2, 8/2, 9/2 or 10/2, and in particular 9/2,
(B1) 180 to 190 parts by weight of hydroxypropylmethylcellulose,
(B2) 19.8 to 22.2 parts by weight of glyceryl behenate,
(C1) 10 to 12 parts by weight of lactose, and
(C2) 10 to 12 parts by weight of colloidal silica; and
a film coating of:
(D) 15 to 45 parts by weight of a substance chosen from shellac, cellulose ethers (in particular HPMC and HPC), and mixtures thereof.

It is recommended to store the composition used according to the invention at a temperature below 40° C., and preferably at a temperature below or equal to 25° C.

The composition comprising magnesium is used according to the invention in combination with a composition intended for treating type 2 diabetes or complications thereof.

The composition intended for treating type 2 diabetes or complications thereof is, according to a particular mode of the invention, a composition for oral administration.

It comprises, in a pharmaceutically acceptable medium, at least one pharmaceutically active agent intended for treating type 2 diabetes or complications thereof.

The pharmaceutically active agent intended for treating type 2 diabetes may be in particular chosen from agents which stimulate insulin secretion, insulin sensitizers, agents which decrease glucogenesis, dipeptidyl peptidase-4 inhibitors and alpha-glucosidase inhibitors.

The agents which stimulate insulin secretion may be chosen in particular from sulfonylureas and "glinides". By way of example of sulfonylureas, mention may in particular be made of carbutamide (Glucidoral®), glibenclamide/glyburide (Daonil®, Euglucan®), glibomuride (Glutril®), gliclazide (Diamicron®), glimepiride (Amarel®) and glipizide (Glibenese®). By way of example of "glinides", mention may in particular be made of repaglinide (NovoNorm®).

The agents which decrease glucogenesis are generally represented by biguanides, and mention may in particular be made of metformin (Glucophage®, Stagid®).

Among the dipeptidyl peptidase-4 inhibitors, mention may in particular be made of saxagliptin, sitaglyptin and vidagliptin.

The insulin sensitizers are represented mainly by thiazolidinediones (TZDs). Mention may in particular be made of pioglitazone (Actos®) or rosiglitazone (Avandia®).

Among the alpha-glucosidase inhibitors, mention may in particular be made of acarbose (Glucor®) or miglitol (Diastabol®).

Diabetic patients are, moreover, known to be a population at risk regarding the development of pathological cardiovascular conditions, in particular atherosclerosis. This is partly due to a greater susceptibility to factors such as hyperlipidemia or hypercholesterolemia. Thus, decreasing the level of low-density lipoprotein-cholesterol (LDL-cholesterol) in the serum is in this respect the first therapeutic approach. It may also be important to identify patients who have a low level of high-density lipoprotein-cholesterol (HDL-cholesterol) and/or high levels of triglycerides. It has in particular been shown that triglyceride-rich lipoproteins originating either from the liver (VLDL) or from the intestine (chylomicron) have a high atherogenic risk.

According to one particular mode of the invention, the composition intended for treating type 2 diabetes or complications thereof may comprise a pharmaceutically active agent chosen from compounds which decrease the lipid or cholesterol level, such as PPARalpha antagonists, in particular fibrates (for example, fenofibrate, bezafibrate, ciprofibrate or gemfibrozyl), inhibitors of HmGCoA (Hydroxymethylglutaryl Coenzyme A reductase), such as statins (for example, atorvastatin, simvastatin or fluvastatin), cholesterol absorption inhibitors (for example, ezetimibe or phytosterols), CETP (Cholesteryl Ester Transfer Protein) inhibitors (for instance, torcetrapib), ACAT (AcylCoA-Cholesterol Acyl Transferase) inhibitors, MTP (Microsomal Triglyceride Transfer Protein) inhibitors, bile acid-sequestering agents (cholestyramine), etc.

According to another particular mode of the invention, the composition intended for treating type 2 diabetes or complications thereof may comprise a pharmaceutically active agent chosen from anti-hypertensive and hypotensive agents, such as ACE (Angiotensin-Converting Enzyme) inhibitors (for instance, captopril, enalapril, ramipril or quinapril), angiotensin II receptor antagonists (for example, losartan, valsartan, telmisartan, eposartan, irbesartan, etc.), beta-blockers (for example, atenolol, metoprolol, labetalol, propranolol), diuretics (for example, furosemide, indapamide, hydrochlorthiazide, or anti-aldosterone), vasodilators such as alpha-receptor blockers (such as prazosin or urapidil) or minoxidil, calcine channel blockers (for instance, nifedipine, felodipine, amlodipine, diltizem or verapamil), etc.

The composition intended for treating type 2 diabetes or complications thereof may comprise at least two pharmaceutically active agents intended for treating type 2 diabetes or complications thereof. Thus, a composition intended for treating type 2 diabetes or complications thereof may comprise, in the same pharmaceutical form or in separate pharmaceutical forms, metformin and a sulfonylurea, a biguanide or a thiazolidinedione. As examples of combinations of active agents, mention may be made of the following products: metformin+glibenclamide/glyburide, metformin+glipizide, metformin+pioglitazone, metformin+rosiglitazone, metformin+sitagliptin, and metformin+vidagliptin. Thus, a composition intended for treating type 2 diabetes or complications thereof may comprise, optionally in the same pharmaceutical form or in several pharmaceutical forms, at least one therapeutic agent for treating type 2 diabetes, as defined above, in particular chosen from agents which stimulate insulin secretion, insulin sensitizers, agents which decrease glucogenesis, alpha-glucosidase inhibitors, and at least one anti-hypertensive or hypotensive agent, as defined above, such as angiotensin II receptor antagonists.

Many pharmaceutical products for treating type 2 diabetes are already on the market. They are generally administered orally.

The present invention therefore makes it possible to treat, in particular to decrease, the effects of type 2 diabetes, and/or to treat at least one of the complications thereof, in particular cardiovascular diseases, hypertension, retinopathy, nephropathy, depression and/or diabetic foot ulcers.

According to one mode of the invention, said compositions are administered simultaneously, separately or in a manner spread out over time. The compositions may therefore be administered simultaneously (but separately), or sequentially.

The term "sequential" is intended to mean an application, separated over time, of the composition comprising the magnesium and the pharmaceutical composition comprising at least one pharmaceutically active agent for treating type 2 diabetes or complications thereof. The user will therefore be able to successively administer the composition comprising the magnesium, and the pharmaceutical composition comprising at least one pharmaceutically active agent for treating diabetes or complications thereof, after a few seconds or after several hours on the same day, in particular within a period ranging from 1 hour to 3 days. According to one alternative, firstly the composition comprising the pharmaceutically active agent for treating type 2 diabetes or complications thereof is administered, and secondly the composition comprising the magnesium is administered. According to another alternative, firstly the composition comprising the magnesium is administered and secondly the pharmaceutical composition comprising at least one pharmaceutically active agent for treating type 2 diabetes or complications thereof is administered.

The pharmaceutical composition comprising at least one pharmaceutically active agent for treating type 2 diabetes or complications thereof will be administered, preferably orally, according to the prescribed treatment, and in particular this treatment will depend on the active agent(s) administered and on the patient.

The composition comprising the magnesium and described above generally comprises between 50 mg and 100 mg of magnesium. Preferably, this composition is administered such that 100 to 500 mg, preferably 100 to 200 mg, of magnesium per day are administered to the subject. Advantageously, one to ten tablets are administered per day, for example in the morning and/or the evening, preferably the morning or the morning and the evening. According to one embodiment, one or two tablets, or even up to 4 or 5 tablets, may be administered once or twice a day. According to another particular embodiment, when the tablet comprises 50 mg of magnesium, from two to four tablets may be administered per day, advantageously in the morning and/or the evening, preferably from two to four tablets only in the morning or alternatively one or two in the morning and one or two in the evening. According to another particular embodiment, when the tablet comprises 100 mg of magnesium, one to two tablets may be administered per day, advantageously in the morning and/or the evening.

In one embodiment, the term "treatment" or "treating" denotes an improvement in or the prophylaxis of type 2 diabetes or in particular one of the complications thereof. In another embodiment, "treatment" or "treating" denotes an improvement in, the prophylaxis of, or the inversion of at least one measurable physical parameter associated with the disease or with the disorder being treated, which is not necessarily discernible in or by the subject treated. In another embodiment, "treatment" or "treating" denotes the inhibition or the slowing down of the progression of type 2 diabetes or one of the complications thereof. In another embodiment, "treatment" or "treating" denotes a delay in the appearance of at least one of the complications of type 2 diabetes, in particular cardiovascular diseases (such as heart rate disorders, arteritis, or atherosclerosis), hypertension, retinopathy, nephropathy, depression or diabetic foot ulcer. In particular, when it is a question of diabetic foot ulcer, the present invention can be adapted to the prevention, a delay in appearance, or a decrease in the risk of developing a diabetic food ulcer.

In one embodiment, the compositions are administered as a curative measure. In the present context, "curative" denotes a reduction in the effects of type 2 diabetes and/or a decrease in the development or worsening of one of the complications of type 2 diabetes, in particular cardiovascular diseases (such as heart rate disorders, arteritis, or atherosclerosis), hypertension, retinopathy, nephropathy, depression and foot ulcers, and more specifically cardiovascular diseases (such as heart rate disorders, arteritis, or atherosclerosis), hypertension, retinopathy, nephropathy and depression.

A subject of the present invention is also a method for treating type 2 diabetes or one of the complications thereof, in which a composition comprising magnesium, as defined above, in combination with a pharmaceutical composition comprising at least one pharmaceutically active agent for treating type 2 diabetes or complications thereof, is administered to a patient suffering from type 2 diabetes and optionally one of the complications thereof, it being possible for said compositions to be administered simultaneously (but separately), or sequentially.

For the purpose of the present invention, the term "patient" or "subject" is intended to mean any mammal, and more particularly a male or female human being.

Other advantages and characteristics of the invention will be understood more clearly on reading the following examples. Of course, these examples are not limiting in nature; they are given solely by way of illustration.

The tests relating to the determination of the Mg dissolution kinetics were carried out at 40° C. in vitro by means of the abovementioned system A: 0.1N HCl medium from T=0 to T=2 h, then buffer medium at pH 6.8 from T=2 h to T=8 h.

Example 1

Tablets (containing a dose of 100 mg of magnesium) having the following formulation (the B1/B2 weight ratio being 9.15/1) were prepared, Amt/tab representing the amount (expressed in mg) of each constituent of the tablet.

| Constituents | Amt/tab (mg) |
| --- | --- |
| Core: | |
| $MgCl_2 \cdot 9/2H_2O$ | 725.0 |
| HPMC | 183.0 |
| Mono-diglyceride behenate | 20.0 |
| Anhydrous lactose | 11.0 |
| Anhydrous colloidal silica | 11.0 |
| Film coating: | |
| Shellac | 39.6 |
| Total: | 989.60 |

The dissolution profile of these tablets is as described in the present invention.

Tablets equivalent to those described in detail above are prepared with $MgCl_2.6/2H_2O$ and $MgCl_2.7/2H_2O$.

Example 2

Tablets (containing a dose of 100 mg of magnesium) having the following formulation (the B1/B2 weight ratio being 9.35/1) were prepared.

| Constituents | Amt/tab (mg) |
| --- | --- |
| Core: | |
| $MgCl_2 \cdot 9/2H_2O$ | 725.0 |
| HPMC | 185.2 |
| Mono-diglyceride behenate | 19.8 |
| Anhydrous lactose | 11.0 |
| Anhydrous colloidal silica | 11.0 |
| Film coating: | |
| Shellac | 39.42 |
| Patent blue | 0.03 |
| Total: | 992.45 |

The dissolution profile of these tablets is as described in the present invention.

Tablets equivalent to those described in detail above are prepared with $MgCl_2.10/2H_2O$ and $MgCl_2.8/2H_2O$.

Example 3

Tablets (containing a dose of 100 mg of magnesium) having the following formulation (the B1/B2 weight ratio being 9.25/1) were prepared.

| Constituents | Amt/tab (mg) |
| --- | --- |
| Core: | |
| $MgCl_2 \cdot 9/2H_2O$ | 725.0 |
| HPMC | 185.0 |
| Mono-diglyceride behenate | 20.0 |
| Anhydrous lactose | 11.0 |
| Anhydrous colloidal silica | 11.0 |
| Film coating: | |
| Shellac | 39.6 |
| Total: | 991.60 |

The dissolution profile of these tablets is as described in the present invention.

Tablets equivalent to those described in detail above are prepared with $MgCl_2.6/2H_2O$ and $MgCl_2.7/2H_2O$.

Example 4

Tablets (containing a dose of 100 mg of magnesium) having the following formulation were prepared according to the abovementioned modes (the B1/B2 weight ratio being 9.15/1).

| Constituents | Amt/tab (mg) |
| --- | --- |
| Core: | |
| $MgCl_2 \cdot 9/2H_2O$ | 725.0 |
| HPMC | 183.0 |
| Mono-diglyceride behenate | 20.0 |
| Anhydrous lactose | 11.0 |
| Anhydrous colloidal silica | 11.0 |
| Film coating 1: | |
| Shellac | 24.17 |
| Film coating 2: | |
| HPMC/HPC mixture 1/3 w/w | 17.514 |
| Patent blue | 0.016 |
| Total: | 991.70 |

The dissolution profile of these tablets is as described in the present invention.

Tablets equivalent to those described in detail above are prepared with $MgCl_2.7/2H_2O$ and $MgCl_2.10/2H_2O$.

Example 5

Tablets (containing a dose of 100 mg of magnesium) having the following formulation (the B1/B2 weight ratio being 9.15/1) were prepared.

| Constituents | Amt/tab (mg) |
| --- | --- |
| Core: | |
| $MgCl_2 \cdot 9/2H_2O$ | 725.0 |
| HPMC | 183.0 |
| Mono-diglyceride behenate | 20.0 |
| Anhydrous lactose | 11.0 |
| Anhydrous colloidal silica | 11.0 |

-continued

| Constituents | Amt/tab (mg) |
|---|---|
| Film coating: | |
| 1st layer: Shellac | 19.8 |
| 2nd layer (external): HPMC/HPC mixture 1/4 w/w | 19.8 |
| Total: | 989.60 |

The dissolution profile of these tablets is as described in the present invention.

Example 6

According to the modes of Example 5, tablets containing 50 mg of magnesium and having, for each constituent, an amount which is half that of the homologous constituent of said Example 5 are prepared.

Example 7

Tablets (containing a dose of 100 mg of magnesium) having the following formulation (the B1/B2 weight ratio being 9.15/1) were prepared.

| Constituents | Amt/tab (mg) |
|---|---|
| Core: | |
| $MgCl_2 \cdot 9/2H_2O$ | 725.0 |
| HPMC | 183.0 |
| Mono-diglyceride behenate | 20.0 |
| Anhydrous lactose | 11.0 |
| Anhydrous colloidal silica | 11.0 |
| Film coating: | |
| 1st layer (internal): HPMC/HPC 1/3 w/w | 19.8 |
| 2nd layer (external): HPMC/HPC mixture 1/4 w/w | 19.8 |
| Total: | 989.60 |

The dissolution profile of these tablets is as described in the present invention.

Tablets equivalent to those described in detail above are prepared with $MgCl_2 \cdot 6/2H_2O$ and $MgCl_2 \cdot 7/2H_2O$.

Example 8

According to the modes of Example 7, tablets containing 50 mg of magnesium and having, for each constituent, an amount which is half that of the homologous constituent of said Example 7 are prepared.

Example 9

Tablets (containing a dose of 100 mg of magnesium) having the following formulation (the B1/B2 weight ratio being 8.8/1) were prepared.

| Constituents | Amt/tab (mg) |
|---|---|
| Core: | |
| $MgCl_2 \cdot 9/2H_2O$ | 725.0 |
| HPMC | 190.0 |
| Mono-diglyceride behenate | 21.5 |
| Anhydrous lactose | 10.0 |
| Anhydrous colloidal silica | 10.0 |
| Pyridoxine hydrochloride | 6.0 |
| Film coating: | |
| Shellac | 40.0 |
| Total: | 1003.0 |

Example 10

Tablets (containing a dose of 50 mg of magnesium) having the following formulation (the B1/B2 weight ratio being 9.15/1) were prepared.

| Constituents | Amt/tab (mg) |
|---|---|
| Core: | |
| $MgCl_2 \cdot 9/2H_2O$ | 362.50 |
| HPMC | 91.50 |
| Mono-diglyceride behenate | 10.00 |
| Anhydrous lactose | 5.50 |
| Anhydrous colloidal silica | 5.50 |
| Film coating 1: | |
| Shellac (Opaglos ® NA715G, product sold by Colorcon) | 1.3 to 2.2%* |
| Film coating 2: | |
| HPMC/HPC mixture 1/3 w/w (Opadry ® VMS, product sold by Colorcon) | 1.1 to 1.6%* |
| Yellow 20A38069 | 0.008 |

Note
*percentage by weight relative to the weight of the bare tablet.

Example 11

Tablets (containing a dose of 50 mg of magnesium) having the following formulation (the B1/B2 weight ratio being 9.15/1) were prepared.

| Constituents | Amt/tab (mg) |
|---|---|
| Core: | |
| $MgCl_2 \cdot 9/2H_2O$ | 362.50 |
| HPMC | 91.50 |
| Mono-diglyceride behenate | 10.00 |
| Anhydrous lactose | 5.50 |
| Anhydrous colloidal silica | 5.50 |
| Film coating: | |
| Shellac (Opaglos ® NA715G, product sold by Colorcon) | 1.7%* |

Note
*percentage by weight relative to the weight of the bare tablet.

The dissolution profile of these tablets is as described in the present invention.

Example 12

Tablets (containing a dose of 50 mg of magnesium) having the following formulation (the B1/B2 weight ratio being 9.15/1) were prepared.

| Constituents | Amt/tab (mg) |
|---|---|
| Core: | |
| $MgCl_2 \cdot 9/2H_2O$ | 362.50 |
| HPMC | 91.50 |
| Mono-diglyceride behenate | 10.00 |
| Anhydrous lactose | 5.50 |
| Anhydrous colloidal silica | 5.50 |
| Film coating 1: | |
| Shellac (Opaglos ® NA715G, product sold by Colorcon) | 1.7* |
| Film coating 2: | |
| HPMC/HPC mixture 1/3 w/w (Opadry ® VMS, product sold by Colorcon) | 0.5%* |

Note
*percentage by weight relative to the weight of the bare tablet.

Example 13

The objective of the clinical study was to evaluate the relative bioavailability of the magnesium provided by two orally administered formulations: 2 tablets containing 50 mg of magnesium (magnesium chloride), such as those described in Example 12, according to the invention, i.e., 100 mg of magnesium element, compared with a reference product, product A (3 immediate-release tablets containing 100 mg of magnesium), i.e., 300 mg of magnesium element.

The randomized clinical study was carried out as a double-blind and cross-over study on healthy subjects (men). Each of the volunteers having participated in the study received the two products being studied, with a 48 h window (wash-out) between the two periods of supplementation.

For the purpose of evaluating the bioavailability, the magnesium in the urine collected between 0 and 24 hours after taking the tablets was assayed in order to measure the amount of magnesium eliminated by the body. A standardized diet provided all the subjects with the same amount of magnesium.

Results

All the subjects were included in the statistical analysis of the results since no piece of atypical or aberrant data was revealed that would have justified excluding them from the analysis.

The main criterion for evaluation of the study was the comparison of the distribution of the total magnesium present in the subject's body, i.e., the "basal" magnesium of the subject, to which was added the magnesium provided by the tablets of Example 12, this being in the urine, compared with the reference product.

The urinary elimination of the magnesium, measured on samples collected sequentially during the 24 hours post-intake, showed homogeneous results, with a power between 73.3% (TO-T5 h) and 96.8% (TO-T24 h).

After 24 hours, the cumulative urinary elimination of the magnesium (i.e., "basal" magnesium+absorbed magnesium) is, following the consumption of 100 mg of magnesium element provided by the tablets according to the invention, 100.53 mg, whereas it is 117.68 mg after the consumption of 300 mg of magnesium element provided by the reference product A.

Urinary Magnesium

The urinary elimination of the magnesium, measured on samples collected sequentially during the 24 hours following the intake of the product, shows homogeneous results.

The statistical power of this study is between 73% and 97%, which means that the number of subjects was sufficient to see any differences between the treatment groups.

These results, presented cumulatively in FIG. 1, show that the product according to the invention with magnesium provision of 100 mg, i.e., 3 times lower than that of the reference product A (300 mg), makes it possible to obtain a urinary magnesium elimination very close to that of product A; the 200 mg of difference between the two doses are not absorbed and are probably eliminated in the feces.

The magnesium absorption yield is therefore better with the product according to the invention than with the reference product.

CONCLUSION

In this study based on the comparison of the urinary elimination of magnesium (which reflects intestinal absorption), the results indicate that the formulation according to the invention makes it possible to obtain a better "bioavailability" of the orally administered magnesium compared with the formulation of the product A.

A Better Bioavailability—a Better Absorption Yield

The results of the study show that the amounts eliminated in the urine are virtually identical with the 100 mg provided by the product according to the invention and with the 300 mg provided by product A, and suggest that the absorption yield is three times higher with the formulation according to the invention and that the difference (approximately 200 mg) was not absorbed and therefore was eliminated in the feces.

An Improvement in Intestinal Tolerance

The greater the amount of magnesium released in the intestine, the more the potential risk of irritation thereof increases, due to the unabsorbed magnesium ions. This irritation can lead to possible digestive disorders such as stomach ache, diarrhea, nausea, etc. Thus, the product according to the invention, by virtue of its low dosage and its better absorption yield, should greatly decrease these risks of adverse effects.

A Better Bioavailability Due to the Formulation According to the Invention

The 100 mg of magnesium provided by the formula according to the invention are found in the urine collected during the 48 hours following the intake, thereby suggesting an excellent bioavailability, capable of maintaining an optimal magnesemia in the long term.

The formulation according to the invention administered at the dose of 100 mg, in comparison with the reference product A containing a dose of 300 mg, therefore allows a better bioavailability, and a better digestive tolerance of the magnesium, which is particularly advantageous for subjects who have or who may have type 2 diabetes or at least one of the complications thereof. The formulation according to the invention in fact allows virtually all of the Mg swallowed to be assimilated by the body for amounts 3 times lower than the reference product, which makes it possible to obtain better intestinal and renal tolerance.

Example 14

The pharmaceutical compositions for oral administration comprising at least one pharmaceutically active agent for treating type 2 diabetes are, for example, chosen from those previously mentioned and sold in particular under the following brand names: Glucophage®, Metformine Biogaran®, Stagid®, Galvus® (active agent INN: Vidagliptin), Glucidoral® (active agent INN: carbutamide), Daonil (active agent INN: glibenclamide), Amarel® (active agent INN: glimepiride), Diamicron® (active agent INN: glicazide), NovoNorm® (active agent INN: repaglinide), Actos® (active agent INN: pioglitazone), Avandia® (active agent INN: rosiglitazone), Glucor® (active agent INN: acarbose), or Diastabol® (active agent INN: miglitol), or else active agent combinations, for instance Glucovance® (active agent INN: metformin+glibenclamide), Competact® (active agent INN: metformin+pioglitazone), Janumet® (active agent INN: metformin+sitagliptin), or Eucreas® (active agent INN: metformin+vidagliptin).

These products can therefore, according to the invention, be administered according to the physician's prescription in combination with the tablets described in one of examples 1-12. Preferably, these products containing magnesium are administered such that 100 to 500 mg of magnesium are administered to the subject per day. Advantageously, one to ten tablets are administered per day, for example in the morning and/or evening, preferably the morning or the morning and the evening. According to one embodiment, one or two tablets, or even up to 4 or 5 tablets, can be administered once or twice a day. According to another particular embodiment, when the tablet comprises 50 mg of magnesium, from two to four tablets can be administered per day, advantageously in the morning and/or evening, preferably from two to four tablets only in the morning or alternatively one or two in the morning and one or two in the evening. According to another particular embodiment, when the tablet comprises 100 mg of magnesium, one to two tablets can be administered per day, advantageously in the morning and/or evening.

The invention claimed is:

1. A method for delaying the onset or progression of long term type 2 diabetes complications selected from diabetic nephropathy, diabetic retinopathy, or diabetic cardiovascular disease comprising orally administering a magnesium matrix composition to a patient in need thereof thereby increasing intestinal and renal tolerance of long-term magnesium intake, wherein said magnesium matrix composition is a tablet consisting of the following components:

a)

| | |
|---|---|
| $MgCl_2 \cdot n(H_2O)$ | 725.0 mg; |
| HPMC | 183.0 mg; |
| mono-diglyceride behenate | 20.0 mg; |
| anhydrous lactose | 11.0 mg; |
| anhydrous colloidal silica | 11.0 mg; | and
a protective coating which slows down the dissolution of the magnesium at the gastric level, where n is a whole or fractional real number greater than 0 and less than or equal to 6;

b)

| | |
|---|---|
| $MgCl_2 \cdot 9/2H_2O$ | 725.0 mg; |
| HPMC | 185.2 mg; |
| mono-diglyceride behenate | 19.8 mg; |
| anhydrous lactose | 11.0 mg; |
| anhydrous colloidal silica | 11.0 mg; | and
a protective coating which slows down the dissolution of the magnesium at the gastric level;

c)

| | |
|---|---|
| $MgCl_2 \cdot 9/2H_2O$ | 725.0 mg; |
| HPMC | 185.0 mg; |
| mono-diglyceride behenate | 20.0 mg; |
| anhydrous lactose | 11.0 mg; |
| anhydrous colloidal silica | 11.0 mg; | and
a protective coating which slows down the dissolution of the magnesium at the gastric level;

d)

| | |
|---|---|
| $MgCl_2 \cdot 9/2H_2O$ | 725.0 mg; |
| HPMC | 183.0 mg; |
| mono-diglyceride behenate | 20.0 mg; |
| anhydrous lactose | 11.0 mg; |
| anhydrous colloidal silica | 11.0 mg; | and
a protective coating which slows down the dissolution of the magnesium at the gastric level; or e)

| | |
|---|---|
| $MgCl_2 \cdot 9/2H_2O$ | 725.0 mg; |
| HPMC | 190.0 mg; |
| mono-diglyceride behenate | 21.5 mg; |
| anhydrous lactose | 10.0 mg; |
| anhydrous colloidal silica | 10.0 mg; |
| pyridoxine hydrochloride | 6.0 mg; | and
a protective coating which slows down the dissolution of the magnesium at the gastric level.

2. The method of claim 1, wherein the protective coating is a film-coating with one or more layers.

3. The method of claim 1, wherein said protective coating is a film-coating with one or more layers and represents 1.3% to 7.5% by weight relative to the weight of the matrix composition.

4. The method of claim 1, wherein said protective coating is:
   (a) a monolayer film-coating of shellac, or
   (b) a two-layer film-coating, each layer comprising a substance chosen from shellac, cellulose ethers, and mixtures thereof.

5. The method of claim 1, wherein said tablet is:
   (I) a tablet with a homogeneous structure containing the magnesium chloride hydrate, or
   (II) a tablet with a composite structure comprising:
      (a) a core structure which is gastroresistant, or housed in a gastroresistant shell, said core structure containing 80% to 40% of the magnesium chloride hydrate, and
      (b) an external layer that is hydrophilic, which dissolves in the stomach and contains 20% to 60% of the magnesium chloride hydrate.

6. The method of claim 1, wherein n is between 2 and 6.

7. The method of claim 1, wherein the magnesium matrix composition is administered in combination with a composition comprising, in a pharmaceutically acceptable medium, at least one pharmaceutically active agent selected from the group consisting of agents which stimulate insulin secretion, insulin sensitizers, agents which decrease glucogenesis, dipeptidyl peptidase-4 inhibitors and alpha-glucosidase inhibitors.

8. The method of claim 7, wherein the composition comprises at least two pharmaceutically active agents.

9. The method of claim 1, said method delaying the onset or progression of diabetic nephropathy.

10. The method of claim 1, said method delaying the onset or progression of diabetic retinopathy.

11. The method of claim 1, said method delaying the onset or progression of diabetic cardiovascular disease.

12. The method of claim 1, wherein n is between 3 and 11/2.

13. The method of claim 1, wherein n is 6/2, 7/2, 8/2, 9/2 or 10/2.

14. The method of claim 1, wherein n is 9/2.

15. The method of claim 7, wherein said magnesium matrix composition and said composition are administered simultaneously, separately or in a manner spread out over time.

* * * * *